(12) United States Patent
Jin et al.

(10) Patent No.: US 11,419,578 B2
(45) Date of Patent: Aug. 23, 2022

(54) ULTRASONIC IMAGING APPARATUS AND METHOD OF CONTROLLING THE SAME

(71) Applicant: SAMSUNG MEDISON CO., LTD., Gangwon-do (KR)

(72) Inventors: Gil Ju Jin, Seoul (KR); Jin Jeon, Seongnam-si (KR); Won Ik Heo, Seoul (KR)

(73) Assignee: SAMSUNG MEDISON CO. LTD., Gangwon-Do (KR)

( * ) Notice: Subject to any disclaimer, the term of this patent is extended or adjusted under 35 U.S.C. 154(b) by 0 days.

(21) Appl. No.: 16/692,256

(22) Filed: Nov. 22, 2019

(65) Prior Publication Data

US 2020/0163648 A1 May 28, 2020

(30) Foreign Application Priority Data

Nov. 22, 2018 (KR) .......................... 10-2018-0145251

(51) Int. Cl.
*A61B 8/00* (2006.01)
*A61B 8/14* (2006.01)

(52) U.S. Cl.
CPC ............ *A61B 8/4444* (2013.01); *A61B 8/145* (2013.01); *A61B 8/54* (2013.01)

(58) Field of Classification Search
CPC ......... A61B 8/4444; A61B 8/145; A61B 8/54; A61B 8/5261; A61B 8/469; A61B 8/465; A61B 8/4416; A61B 8/4461; A61B 8/42; A61B 8/085
See application file for complete search history.

(56) References Cited

U.S. PATENT DOCUMENTS

| | | | |
|---|---|---|---|
| 2007/0239009 A1* | 10/2007 | Kasashima et al. ...... | A61B 8/00 |
| 2015/0182191 A1* | 8/2015 | Caluser et al. ....... | A61B 8/4254 |
| 2016/0030003 A1* | 2/2016 | Liu .......................... | A61B 8/54 600/440 |
| 2016/0095573 A1* | 4/2016 | Tanaka et al. ........... | A61B 8/06 |
| 2017/0196532 A1* | 8/2017 | Choi ........................ | A61B 8/00 |
| 2019/0175947 A1* | 6/2019 | Patch .................... | A61N 5/1067 |

FOREIGN PATENT DOCUMENTS

| | | |
|---|---|---|
| EP | 3 192 447 A1 | 7/2017 |
| WO | 2016/175758 A2 | 11/2016 |

OTHER PUBLICATIONS

Extended European Search Report issued in corresponding European Patent Application No. 19210849.6 dated Apr. 6, 2020.

* cited by examiner

*Primary Examiner* — Joseph M Santos Rodriguez
*Assistant Examiner* — Kaitlyn E Sebastian
(74) *Attorney, Agent, or Firm* — Morgan, Lewis & Bockius LLP

(57) ABSTRACT

An ultrasonic imaging apparatus includes: an ultrasonic probe configured to transmit an ultrasonic signal to an object and receive an echo signal reflected from the object; a display configured to output an ultrasound image output by the ultrasonic probe and a medical image having a modality different from that of the ultrasound image in a matched state; an inputter configured to receive a user input for adjusting a range of an output area of the medical image; and a controller configured to control an ultrasonic beam of the ultrasonic probe to adjust an output area of the ultrasound image in response to detecting that the output area of the medical image is adjusted by the user input.

18 Claims, 11 Drawing Sheets

ULTRASONIC IMAGING APPARATUS AND METHOD OF CONTROLLING THE SAME

CROSS-REFERENCE TO RELATED APPLICATION(S)

This application is based on and claims priority under 35 U.S.C. § 119 to Korean Patent Application No. 10-2018-0145251, filed on Nov. 22, 2018 in the Korean Intellectual Property Office, the disclosure of which is incorporated by reference in its entirety.

TECHNICAL FIELD

Embodiments of the disclosure relate to an ultrasonic imaging apparatus and a method of controlling the ultrasonic imaging apparatus, and more particularly, to an ultrasonic imaging apparatus that matches ultrasound images with medical images having different modalities, and a method of controlling the ultrasonic imaging apparatus.

BACKGROUND

An ultrasonic imaging apparatus irradiates ultrasonic waves to an object and detects echo signals reflected from the object to generate images of a target part inside the object such as tomographic or blood flow of soft tissues, thereby providing information of a required target part.

Although the ultrasound imaging apparatus has an advantage of obtaining a real time image, it has a disadvantage that it is difficult to identify an outline, an internal structure, or a lesion of an organ because it contains a large number of noises.

Recently, in order to overcome the above-described disadvantages, medical images obtained from other medical apparatuses are matched with ultrasound images and provided. For example, a Magnetic Resonance Imaging (MRI) apparatus, which provide relatively free imaging conditions and provide excellent contrast and various images in soft tissues or a higher resolution a Computerized Tomography (CT) scanner and ultrasound images are matched and provided.

SUMMARY

Therefore, it is an aspect of the disclosure to provide an ultrasonic imaging apparatus capable of providing an image in which an ultrasound image and a medical image are matched with each other, and a method of controlling the ultrasonic imaging apparatus.

It is another aspect of the disclosure to provide an ultrasonic imaging apparatus capable of providing a guide image that can determine a position of an object, and a method of controlling the ultrasonic imaging apparatus.

Additional aspects of the disclosure will be set forth in part in the description which follows and, in part, will be obvious from the description, or may be learned by practice of the disclosure.

In accordance with an aspect of the disclosure, an ultrasonic imaging apparatus includes: an ultrasonic probe configured to transmit an ultrasonic signal to an object and receive an echo signal reflected from the object; a display configured to output an ultrasound image output by the ultrasonic probe and a medical image having a modality different from that of the ultrasound image in a matched state; an inputter configured to receive a user input for adjusting a range of an output area of the medical image; and a controller configured to control an ultrasonic beam of the ultrasonic probe to adjust an output area of the ultrasound image in response to detecting that the output area of the medical image is adjusted by the user input.

The ultrasonic image may output in real time by controlling only the ultrasonic beam while the ultrasonic probe is fixed to the object.

The controller may control the ultrasound beam to move in a lateral direction when detecting the user input of moving the output area of the medical image in a left direction or a right direction.

The controller may control the ultrasound beam to adjust a depth of an axis direction when detecting the user input of moving the output area of the medical image in an upward direction or a downward direction.

The controller may control the ultrasound beam to move or rotate in an elevation direction when detecting the user input of moving to an adjacent tomographic plane with respect to a tomographic plane of the output area of the medical image.

The controller may control the ultrasound beam by changing at least one of element operation, steering, beam forming, and focusing of the ultrasonic probe.

The ultrasonic imaging apparatus may further include: a storage configured to store the medical image. The medical image may include at least one of Magnetic Resonance Imaging (MRI), Computerized Tomography (CT), Positron Emission Tomography (PET), and Single Photon Tomography Computed Tomography (SPECT) that three-dimensional (3D) volume image data.

The display may output a guide image. The controller may generate the guide image in which an output limit range of the medical image of the object, an output limit range of the ultrasound image of the object, and a position area indicating a position of a current ultrasound image of the object are displayed.

When a movement of the ultrasonic probe with respect to the object is detected, the controller may change the position of the output limit range of the ultrasound image.

The controller may generate a warning notification when the output area of the medical image according to the user input is an area that the ultrasonic probe cannot photograph.

The controller may control the position area displayed on the guide image to be moved according to the user input of moving the output area of the medical image.

The controller may control the position area to be moved along a lateral direction when the output area of the medical image moves in a left direction or a right direction.

The controller may control the position area to be moved along an axial direction when the output area of the medical image moves upward or downward.

The controller may control the position area to be moved or rotated in an elevation direction when the output area of the medical image moves an adjacent tomographic plane with respect to a tomographic plane.

In accordance with another aspect of the disclosure, a method of controlling an image performed by an ultrasonic imaging apparatus, the method includes: outputting an ultrasound image of an object output by an ultrasonic probe and a medical image of the object having a modality different from that of the ultrasound image in a matched state; receiving a user input of moving an output area of the medical image; and controlling an ultrasonic beam of the ultrasonic probe to adjust an output area of the ultrasound image in response to detecting that the output area of the medical image is adjusted by the user input.

The ultrasonic image may output in real time by controlling only the ultrasonic beam while the ultrasonic probe is fixed to the object.

The controlling of the ultrasonic beam may include controlling the ultrasound beam to move in a lateral direction when detecting the user input of moving the output area of the medical image in a left direction or a right direction.

The controlling of the ultrasonic beam may include controlling the ultrasound beam to adjust a depth of an axis direction when detecting the user input of moving the output area of the medical image in an upward direction or a downward direction.

The controlling of the ultrasonic beam may include controlling the ultrasound beam to move or rotate in an elevation direction when detecting the user input of moving to an adjacent tomographic plane with respect to a tomographic plane of the output area of the medical image.

The controlling of the ultrasonic beam may include controlling the ultrasound beam by changing at least one of element operation, steering, beam forming, and focusing of the ultrasonic probe.

The medical image may include at least one of Magnetic Resonance Imaging (MRI), Computerized Tomography (CT), Positron Emission Tomography (PET), and Single Photon Tomography Computed Tomography (SPECT) that three-dimensional (3D) volume image data.

The outputting of the ultrasound image of the object output by the ultrasonic probe and the medical image of the object having the modality different from that of the ultrasound image in the matched state may include outputting a guide image. The guide image may display an output limit range of the medical image of the object, an output limit range of the ultrasound image of the object, and a position area indicating a position of a current ultrasound image of the object.

The outputting of the guide image may include changing the position of the output limit range of the ultrasound image when a movement of the ultrasonic probe with respect to the object is detected.

The outputting of the guide image may include generating a warning notification when the output area of the medical image according to the user input is an area that the ultrasonic probe cannot photograph.

The outputting of the guide image may include controlling the position area displayed on the guide image to be moved according to the user input of moving the output area of the medical image.

The outputting of the guide image may include controlling the position area to be moved along a lateral direction when the output area of the medical image moves in a left direction or a right direction.

The outputting of the guide image may include controlling the position area to be moved along an axial direction when the output area of the medical image moves upward or downward.

The outputting of the guide image may include controlling the position area to be moved or rotated in an elevation direction when the output area of the medical image moves an adjacent tomographic plane with respect to a tomographic plane.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Figure 1:
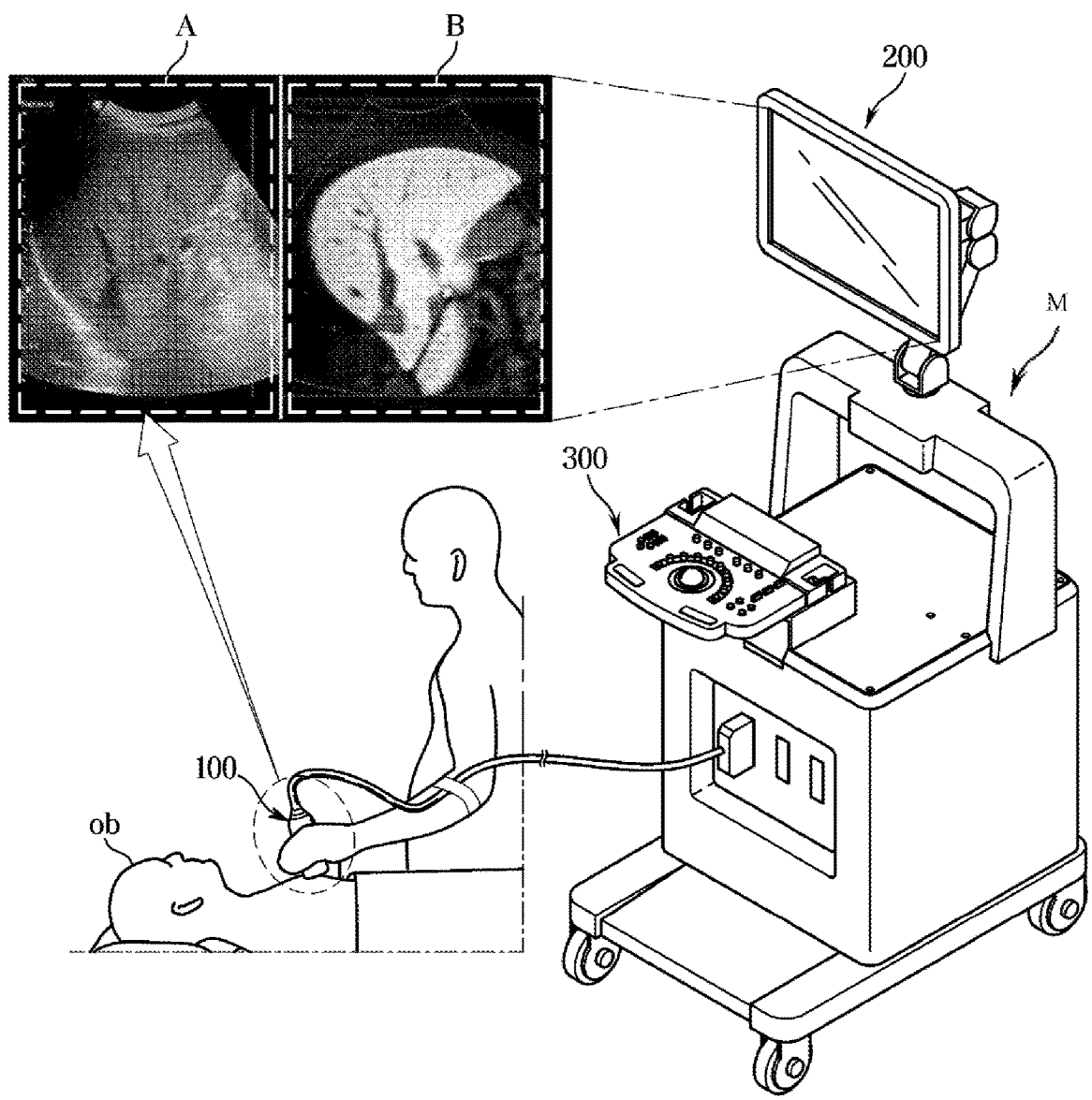
FIG. 1 is a view illustrating a matched image provided by an ultrasound imaging apparatus and the ultrasound imaging apparatus according to embodiments of the disclosure.

Like reference numerals refer to like elements throughout the specification. Not all elements of embodiments of the disclosure will be described, and description of what are commonly known in the art or what overlap each other in the embodiments will be omitted. The terms as used throughout the specification, such as "~ part," "~ module," "~ member," "~ block," etc., may be implemented in software and/or hardware, and a plurality of "~ parts," "~ modules," "~ members," or "~ blocks" may be implemented in a single element, or a single "~ part," "~ module," "~ member," or "~ block" may include a plurality of elements.

It will be understood that when an element is referred to as being "connected" to another element, it can be directly or indirectly connected to the other element, wherein the indirect connection includes "connection" via a wireless communication network.

Also, when a part "includes" or "comprises" an element, unless there is a particular description contrary thereto, the part may further include other elements, not excluding the other elements.

Further, when it is stated that a layer is "on" another layer or substrate, the layer may be directly on another layer or substrate or a third layer may be disposed therebetween.

It will be understood that, although the terms first, second, third, etc., may be used herein to describe various elements, it should not be limited by these terms. These terms are only used to distinguish one element from another element.

As used herein, the singular forms "a," "an" and "the" are intended to include the plural forms as well, unless the context clearly indicates otherwise.

An identification code is used for the convenience of the description but is not intended to illustrate the order of each step. Each of the steps may be implemented in an order different from the illustrated order unless the context clearly indicates otherwise.

Prior to the description of the specification, some terms used in the specification will be clarified.

An object may indicate organs of a human body, fetus, animals, metal, nonmetal, or some parts thereof. For example, the object may include organs of the human body (e.g., a liver, a heart, a uterus, a brain, a breast, an abdomen) or blood vessels.

An ultrasonic image may refer to an image of the object to be obtained using ultrasonic waves. At this time, the ultrasonic image may be a two-dimensional (2D) image or a three-dimensional (3D) image. The ultrasonic image has an advantage of providing an internal image of the object in real time A medical image may be an image obtained from an ultrasound imaging apparatus and other medical diagnosis apparatuses, and may refer to an image having a modality different from that of the ultrasound image. For example, the medical images may include Magnetic Resonance Imaging (MRI), Computerized Tomography (CT), Positron Emission Tomography (PET), and Single Photon Tomography Computed Tomography (SPECT).

Hereinafter, the operation principles and embodiments of the disclosure will be described with reference to the accompanying drawings.

FIG. 1 is a view illustrating a matched image provided by an ultrasound imaging apparatus and the ultrasound imaging apparatus according to embodiments of the disclosure.

Referring to FIG. 1, an ultrasound imaging apparatus 1 may include an ultrasonic probe 100, a display 200, an inputter 300, and a main body M.

The ultrasonic probe 200 configured to contact an object ob may transmit and receive ultrasonic signals to or from the object ob. In more detail, the ultrasonic probe 200 may generate ultrasonic signals according to input pulses, may transmit the generated ultrasonic signals to the inside of the object ob, and may receive echo ultrasonic signals reflected from a specific part of the object ob.

Particularly, the ultrasound probe 100 may transmit a focused ultrasound beam to the object ob along a transmission scan line by appropriately delaying an input time of pulses input to each of the conversion elements. Meanwhile, the ultrasonic echo signals reflected from the object ob may be input to each of the conversion elements with different reception times. Each of the conversion elements may output the input ultrasonic echo signals. In the disclosure, the ultrasound probe 100 may be a 2D matrix probe, a 3D volume probe, or a 2D tomographic probe, but is not limited thereto.

Meanwhile, the ultrasonic probe 100 may transmit and receive and control an ultrasonic beam in a state being fixed to the object ob as illustrated in FIG. 1. Particularly, the display 200 may simultaneously output the ultrasound image and the medical image, and the user may adjust an output area of the medical image through the inputter 300. The ultrasound image may be matched according to the medical image that is adjusted by the user, and the ultrasound image may be matched with the medical image through various controls such as element operation, steering, beam forming and focusing, and the like of the ultrasonic probe 100.

The display 200 may be provided in the main body M, and may simultaneously or separately output an ultrasound image A and a medical image B. The ultrasound image A may represent a real time sectional image at the same position as a sectional image output from the medical image B when the output area of the medical image B is changed by a user input.

The display 200 may be implemented in various ways that can be provided visual information to the user, such as a cathode ray tube (CRT), a liquid crystal display (LCD), a light emitting diode (LED), a plasma display panel (PDP), an organic light emitting diode (OLED), and the like. Of course, it is not limited to the above-described examples.

The inputter 300 may be provided in the main body M for the user to control the ultrasound imaging apparatus 1. The inputter 300 may receive various control commands, such as a command regarding an operation sequence of the ultrasonic probe 100 from the user. Further, the inputter 300 may receive an input that changes a tomographic position appearing in the output area of the medical image by moving the coordinates of 3D volume data representing the medical image (B). In addition, the inputter 300 may receive various commands for controlling the ultrasound imaging apparatus 1 and various apparatuses connected to the ultrasound imaging apparatus 1

Meanwhile, the inputter 300 may be implemented by a keyboard or a touch panel method. For example, the keyboard may be implemented in hardware. The keyboard may include at least one of a switch, a key, a joystick, and a trackball. As another example, the keyboard may be implemented in software such as a graphical user interface. In this case, the keyboard may be implemented as the touch panel through the display 200. When the keyboard is implemented as the touch panel, the user may input the control command through a touch input. The touch panel may be implemented, for example, a liquid crystal display (LCD) panel, a light emitting diode (LED) panel, an organic light emitting diode (OLED) panel, or the like.

Figure 2:
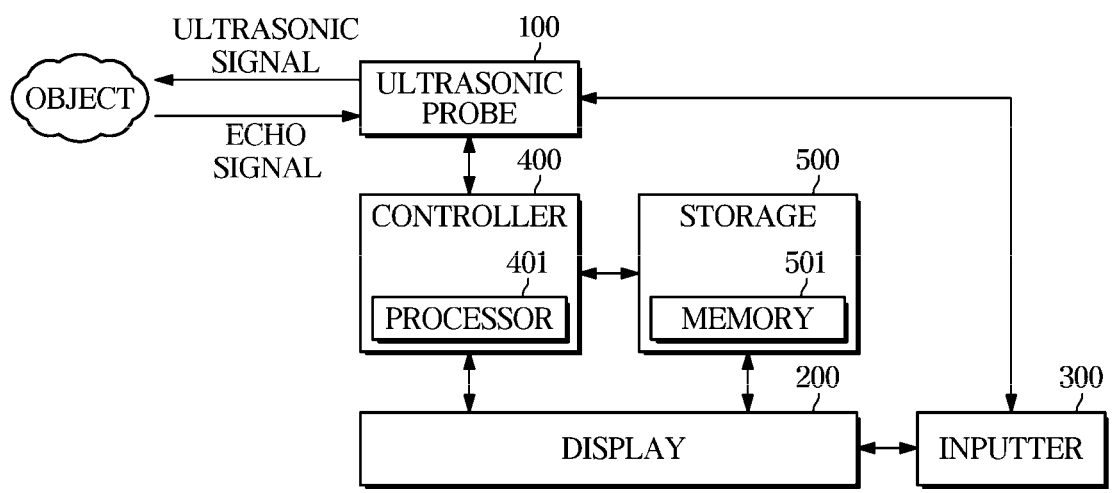
FIG. 2 is a control block diagram of an ultrasound imaging apparatus according to embodiments of the disclosure.

FIG. 2 is a control block diagram of an ultrasound imaging apparatus according to embodiments of the disclosure.

Referring to FIG. 2, the ultrasound imaging apparatus 1 may include the ultrasonic probe 100, the display 200, the inputter 300, a controller 400, and a storage 500.

The ultrasonic probe 100 may transmit the ultrasonic signal to the object ob and receive the reflected echo signal. For this purpose, the ultrasonic probe 100 may include a transducer (not shown). Here, the transducer may refer to an apparatus for converting a certain type of energy into another type of energy. For example, the transducer may convert electrical energy into wave energy and may convert wave energy into electrical energy.

On the other hand, the ultrasonic probe 100 may irradiate the ultrasonic signal according to a control command signal. To this end, the ultrasonic probe 100 may include a transducer module for converting the electrical signal and the ultrasonic signal according to the control command. The transducer may be implemented as a one-dimensional or two-dimensional transducer array.

The transducer may define three directions that are perpendicular to the center in an axial direction A, a lateral direction L, and an elevation direction E, respectively. Particularly, a direction in which the ultrasonic signal is emitted may be defined as the axial direction A. A direction in which transducers are arranged in a row may be defined as the lateral direction L. A direction perpendicular to the axial direction A and the lateral direction L may be defined as the elevation direction E.

When the output area of the medical image is changed according to the user input received through the inputter 300, the controller 400 may control the ultrasound beam transmitted and received by the ultrasonic probe 100 to output the ultrasonic image of the tomographic position of the object such as the output area of the medical image.

Meanwhile, the ultrasound image output in real time by controlling the ultrasound beam through the medical image will be described in detail with reference to FIGS. 3 and 4.

Figure 3:
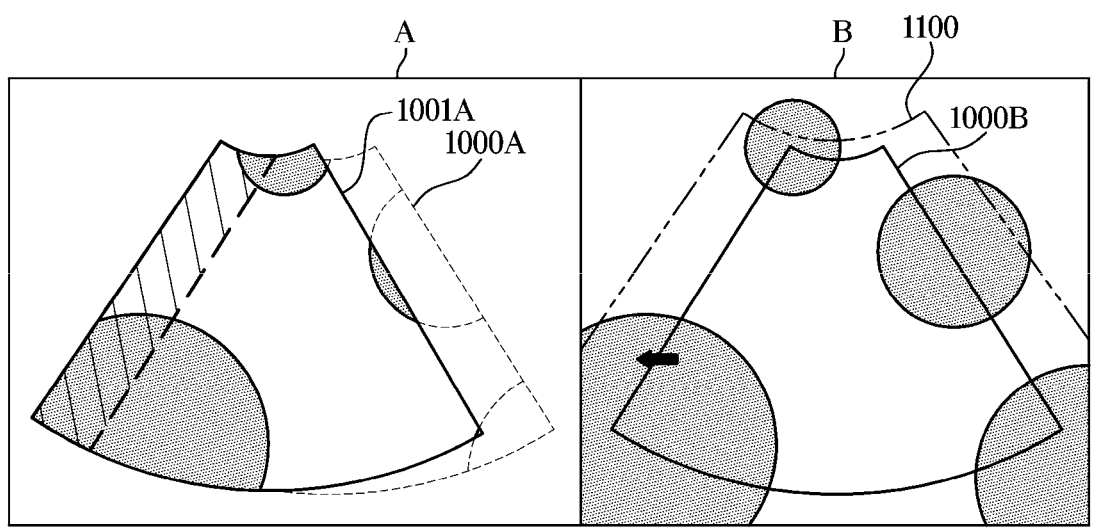
FIGS. 3 and 4 are views for describing a process of controlling an ultrasound image according to a user input.
Figure 4:
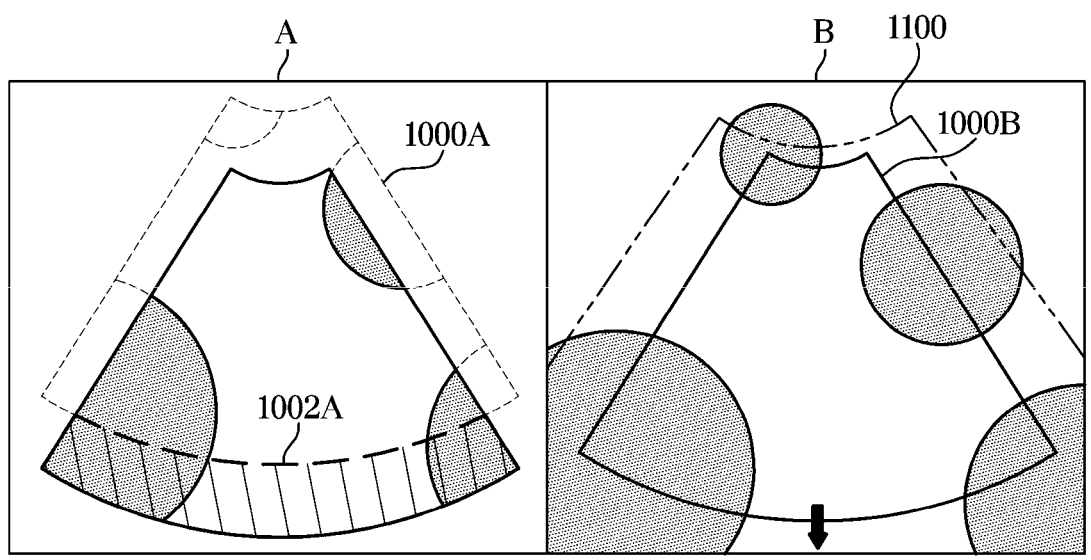

Referring to FIGS. 3 and 4, the display 200 may output the ultrasound image A on the left side and the medical image B on the right side. The controller 400 may output the ultrasound image A and the medical image B, and may perform matching. The order of the illustrated images is only an example and may be based on various arrangements according to user settings.

For example, the medical images may include the Magnetic Resonance Imaging (MRI), the Computerized Tomography (CT), the Positron Emission Tomography (PET), and the Single Photon Tomography Computed Tomography (SPECT).

The medical images B may include at least one of the Magnetic Resonance Imaging (MRI), the Computerized Tomography (CT), the Positron Emission Tomography (PET), and the Single Photon Tomography Computed Tomography (SPECT), and may be the image stored as 3D volume image data. Therefore, various tomographic planes of the object may be identified according to the user's command.

In addition, the ultrasound image A, which is deformed according to the user input, may be deformed by controlling any one of the element operation, the steering operation, the beamforming operation, and the focusing operation of the ultrasonic probe 100.

Referring to FIG. 3, the user may input a movement command to the inputter 300 to move the output area of the medical image B on the right side. For example, when the user inputs a command to move a current output area 1000B of the medical image B to the left, the output area on the left side may be output from the center of the medical image B based on the currently output area. In addition, the medical image B may also display an ultrasound image output limit line 1100 indicating a range in which the ultrasound image A can be output.

As described above, when the user inputs the command to move the current output area 1000B of the medical image B to the left, the controller 400 may control the ultrasonic beam transmitted and received by the ultrasonic probe 100 to move in the lateral direction. Therefore, the output area of the ultrasound image may be moved from the first output area 1000A to a second output area 1001A. The second output area 1001A may be positioned at the center of the ultrasound image A and output in a state being matched with the medical image B.

Referring to FIG. 4, the user may input a movement command to the inputter 300 to move the output area of the medical image B on the right side. For example, when the user inputs the command to move the current output area 1000B of the medical image B downward, the lower output area may be output from the center of the medical image B based on the currently output area. In addition, the medical image B may also display the ultrasound image output limit line 1100 indicating a range in which the ultrasound image A can be output.

As described above, when the user inputs the command to move the current output area 1000B of the medical image B downward, the controller 400 may control the ultrasonic beam transmitted and received by the ultrasonic probe 100 to adjust a depth in the axial direction. Therefore, the output area of the ultrasound image may be moved from the first output area 1000A to a second output area 1002A. The second output area 1002A may be positioned at the center of the ultrasound image A and output in a state being matched with the medical image B.

The controller may generate a warning notification when the output area of the medical image according to the user's movement input is an area that the ultrasonic probe 100 cannot photograph. This is because the medical image is the image obtained through pre-stored 3D volume image data, and the ultrasound image is the image obtained while the ultrasonic probe 100 is fixed to the object, and thus the range of the tomographic plane that can be output is using different characteristics. For example, when the user input for the medical image is outside the area where the fixed ultrasonic probe 100 is obtainable, the controller 400 may display a notification indicating that the ultrasonic probe needs to be moved on the display 200 or generate a warning sound to notify the user.

In addition, when the user inputs the command to move the output area of the medical image B to another tomographic plane, the controller 400 may control to move or rotate the ultrasonic beam transmitted and received by the ultrasonic probe 100 in the elevation direction.

In the above, specific principles and various embodiments of deforming the ultrasound image A as the medical image B is deformed in the matched image have been described. However, when the ultrasound image A is manipulated only through the medical image B, it is difficult to determine the position of the object. In addition to the ultrasound image A and the medical image B on an output screen of the display 200, a method of providing a convenience for diagnosis by outputting a guide image 2000 together may be adopted. Hereinafter, the guide image 2000 will be described in detail with reference to FIGS. 5 to 9.

Figure 5:
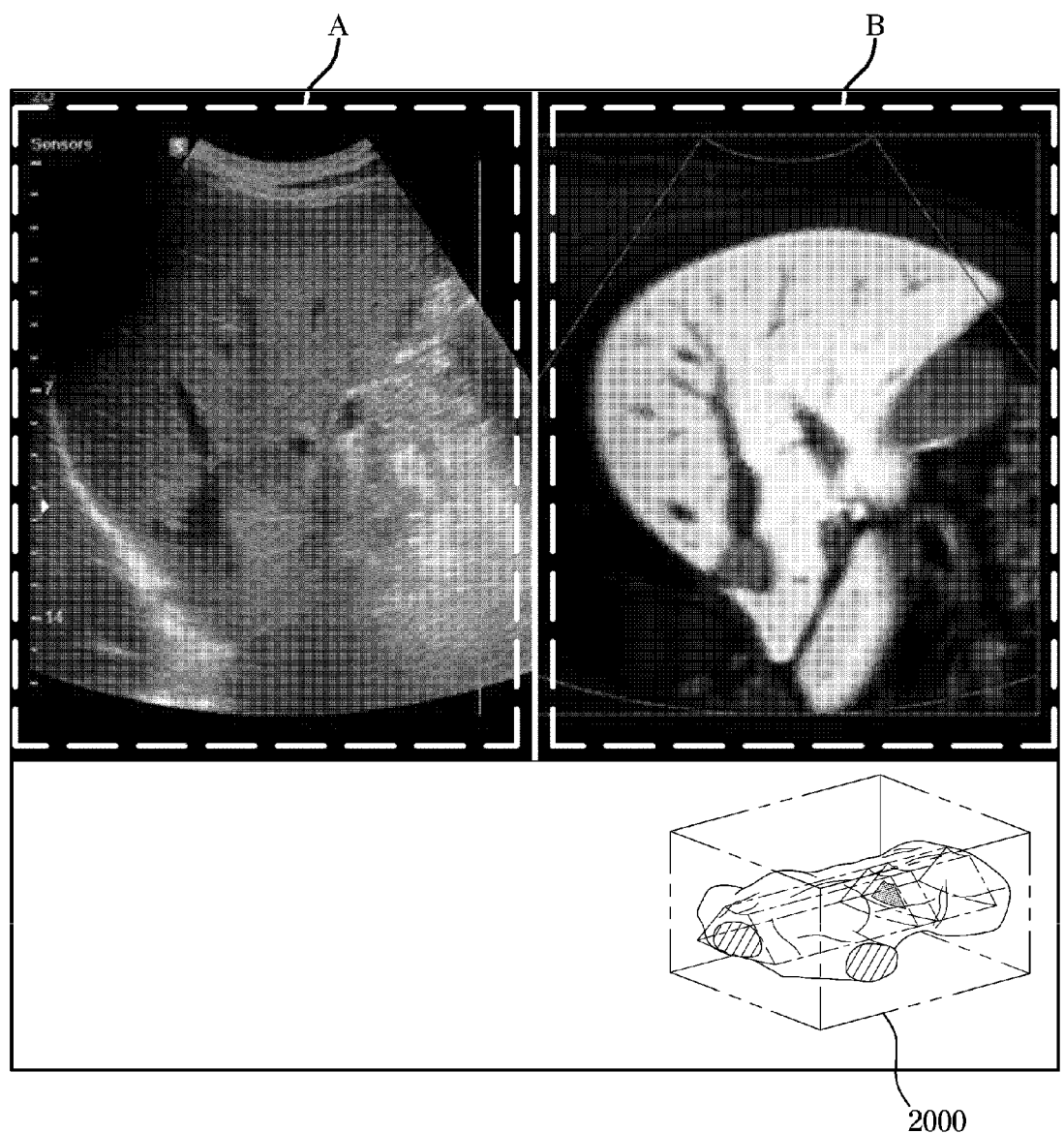
FIG. 5 is a view illustrating an ultrasound image, a medical image, and a guide image provided according to embodiments of the disclosure.

As illustrated in FIG. 5, the guide image 2000 may be output together with the ultrasound image A and the medical image B. The guide image 2000 may be generated based on the 3D volume data of the stored medical image B. The guide image 2000 may display an output limit range of the medical image of the object, an output limit range of the ultrasound image of the object, and a position area indicating a position of the current ultrasound image of the object.

When the user inputs the movement command to the inputter 300 to move the output area through the medical image B, the position area displayed on the guide image 2000 may be moved to correspond to the movement command.

Figure 6:
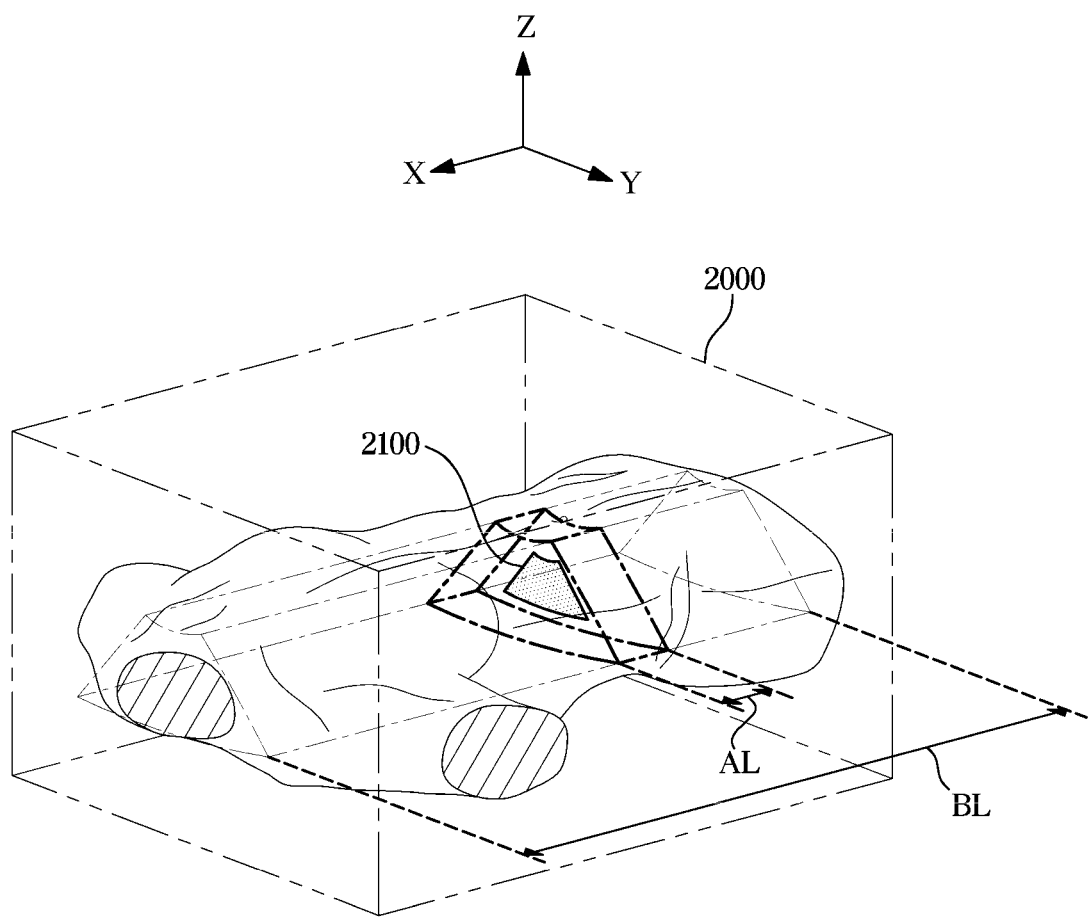
FIGS. 6 to 10 are views for describing the guide image of FIG. 5 in more detail.

Referring to FIG. 6, the guide image 2000 may display at least one of an output limit range BL of the medical image of the object, an output limit range AL of an ultrasound image, and a position area 2100. Hereinafter, for convenience of description, the output limit range AL of the ultrasound image is described as a first limit range, and the output limit range BL of the medical image is described as a second limit range.

The first limit range may represent a range in which the ultrasonic image can be obtained by controlling the ultrasonic beam while the ultrasonic probe 100 is fixed to the object. The second limit range may represent a range of the medical image that can be extracted from the stored 3D volume data. The position area 2100 is a position where the ultrasonic beam of the ultrasonic probe 100 is irradiated, and the tomographic plane corresponding to the position area 2100 is output to the ultrasound image.

As described above, the ultrasonic beam of the ultrasonic probe 100 may be controlled in three directions. Here, the three directions may be defined as the axial direction A, the lateral direction L, and the elevation direction E, respectively. Particularly, the direction in which the ultrasonic signal is irradiated may be defined as the axial direction A. The direction in which transducers are arranged in the row may be defined as the lateral direction L. The direction perpendicular to the axial direction A and the lateral direction L may be defined as the elevation direction E. According to FIG. 6, the axial direction A may be set as a Z-axis direction, the lateral direction L may be set as a Y-axis direction, and the elevation direction E may be set as the X-axis direction in the guide image 2000.

Meanwhile, the fixed ultrasonic probe 100 may obtain the ultrasound image at another position of the object. At this time, as the ultrasonic probe 100 moves, the range in which the ultrasonic probe 100 can obtain the image is changed.

Therefore, the first limit range output from the guide image 2000 needs to be changed. Accordingly, when the controller 400 detects the movement of the ultrasonic probe 100 with respect to the object, the controller 400 may control to change the position of the output limit range of the ultrasonic image output in the guide image 2000.

Figure 7:
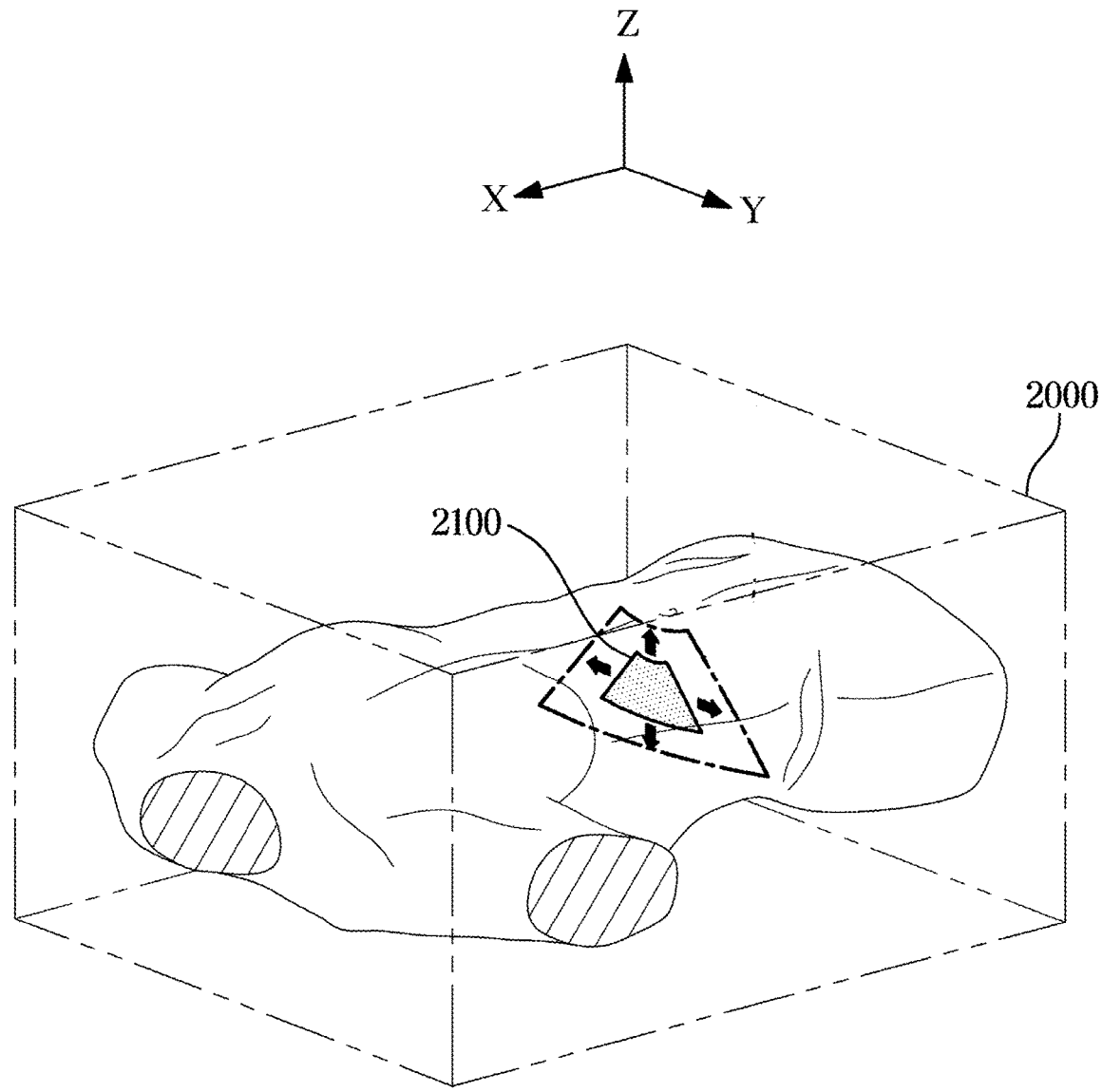

Referring to FIG. 7, when the user inputs the movement command to the inputter 300 to move the output area of the medical image B, the position area 2100 of the guide image 2000 may be moved to indicate the position of the object of the ultrasound beam moved according to the movement command.

In an embodiment, when the user inputs the command to move the output area of the medical image B in the left direction or the right direction, the ultrasonic beam transmitted and received by the ultrasonic probe 100 may be controlled to move in the lateral direction L, and the position area 2100 the guide image 2000 may be moved in the left or right direction along the Y-axis direction. The user may identify the position of the tomographic plane of the object through the moving position area in the guide image 2000.

In another embodiment, when the user inputs the command to move the output area of the medical image B upward or downward, the ultrasonic beam transmitted and received by the ultrasonic probe 100 may be controlled to move along the axial direction, and the position area 2100 of the guide image.2000 may be moved in the upward or downward direction along the Z-axis direction.

Figure 8:
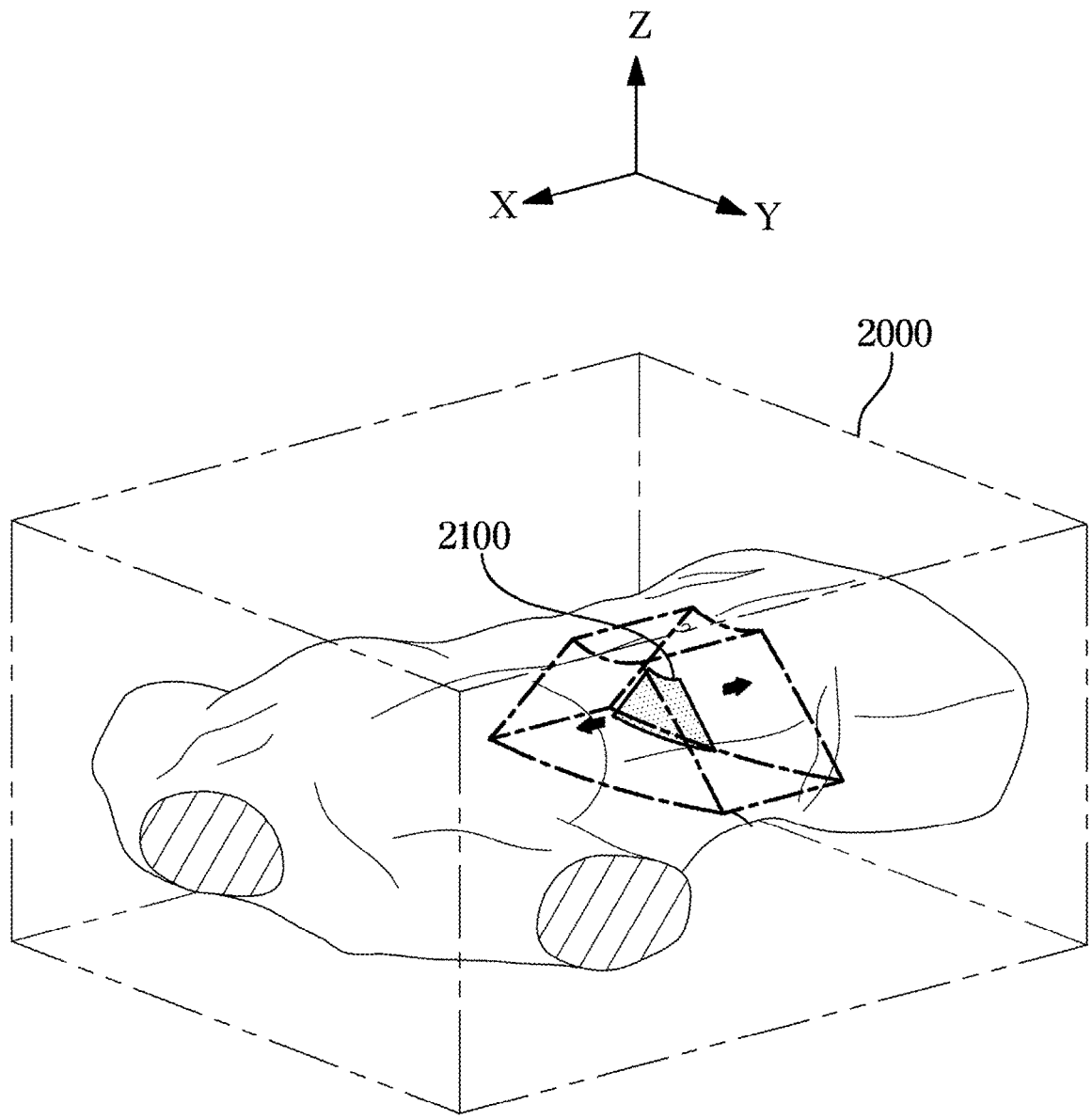

Referring to FIG. 8, when the user inputs the movement command to the inputter 300 to move to an adjacent tomographic plane perpendicular to the output tomographic plane of the medical image B, the position area 2100 of the guide image 2000 may be moved to indicate the position of the object of the ultrasound beam moved according to the movement command.

In an embodiment, when the user inputs the command to move to the adjacent tomographic plane perpendicular to the output tomographic plane of the medical image B, the ultrasonic beam transmitted and received by the ultrasonic probe 100 may be controlled to move along the elevation direction E, and the position area 2100 the guide image 2000 may be moved along the X-axis direction. In the disclosure, when the irradiation area of the ultrasonic beam moves side by side along the object plane, the position area 2100 may be also moved side by side the guide image 2000.

Figure 9:
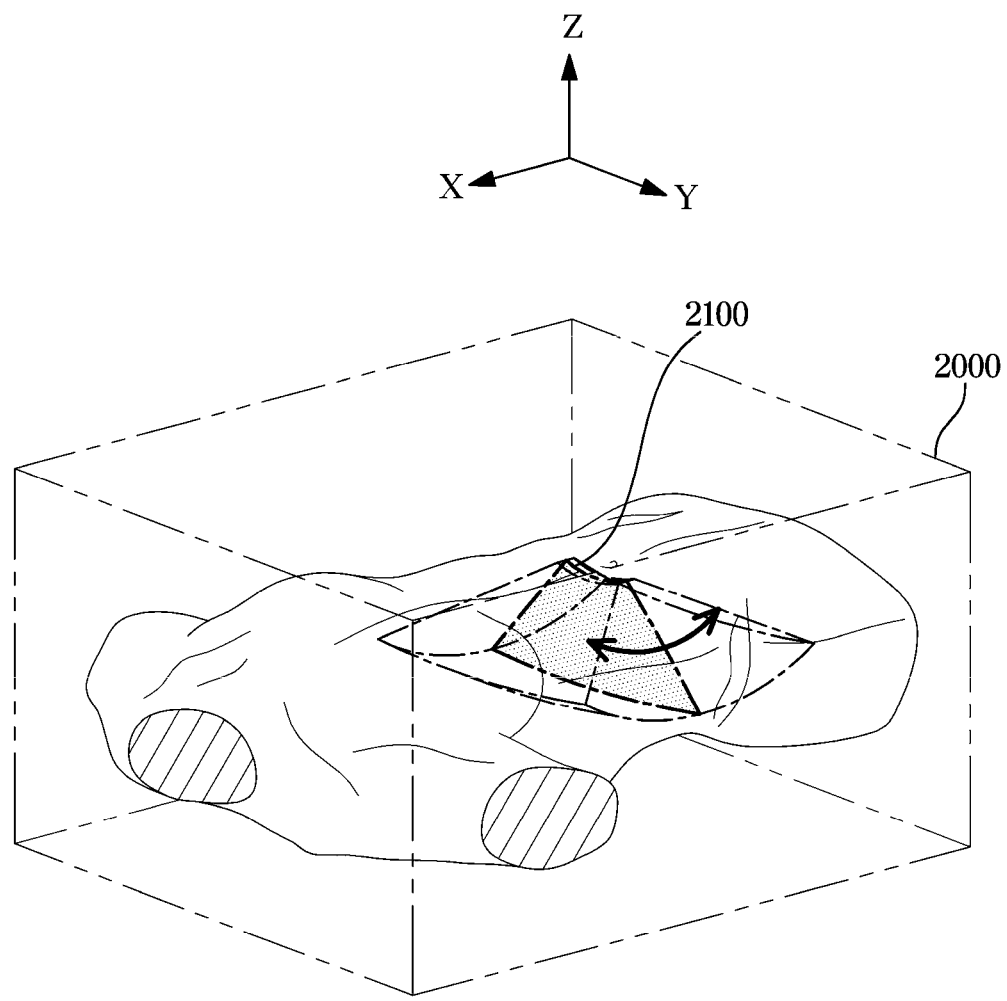

On the other hand, according to another embodiment, the ultrasonic probe 100 may further include a driver configured to driving to swing an element for transmitting and receiving the ultrasonic beam. In this case, the driver may be a stepping motor that can control a rotation angle. Therefore, the ultrasonic probe 100 may swing the ultrasonic beam in the elevation direction E with respect to the object. Referring to FIG. 9, when the user inputs the command to swing the output tomographic plane of the medical image B, the ultrasonic beam transmitted and received by the ultrasonic probe 100 may be controlled to swing along the elevation direction E, and the position area 2100 of the guide image 2000 may be rotated based on the Y-axis.

Figure 10:
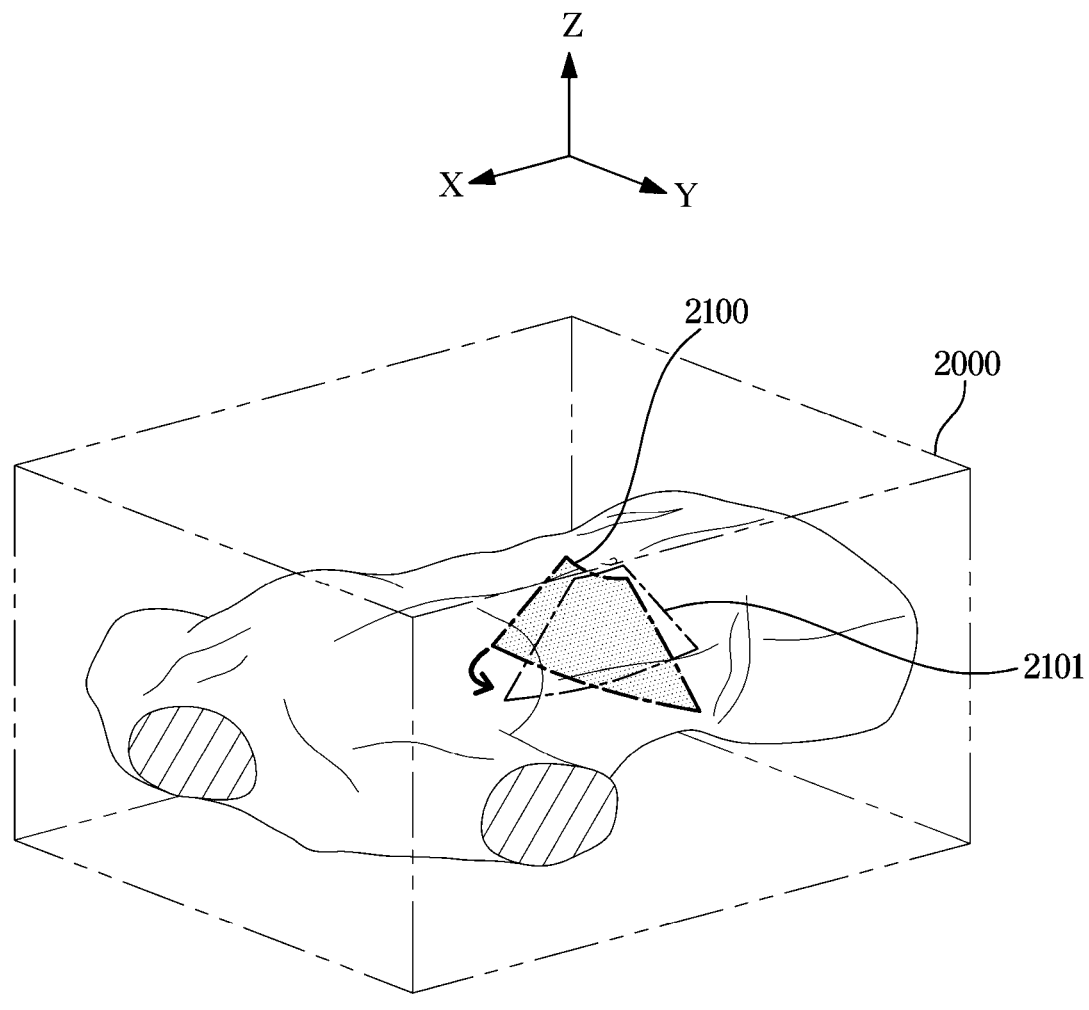

Referring to FIG. 10, the position area 2100 of the guide image 2000 may be rotated based on the Z-axis. This indicates the case where the ultrasonic probe 100 obtains the tomographic plane in a diagonal direction with respect to the object. For example, when the ultrasonic probe 100 is the 2D matrix probe, the position or rotation angle at which the ultrasonic beam is transmitted and received may be variously controlled by controlling the operation of the element. When the user inputs the command to rotate the output tomographic plane of the medical image B, by controlling the operation of the element, as illustrated in FIG. 10, the position area 2100 of the guide image 200 may be changed to the rotated rotation area 2101.

Figure 11:
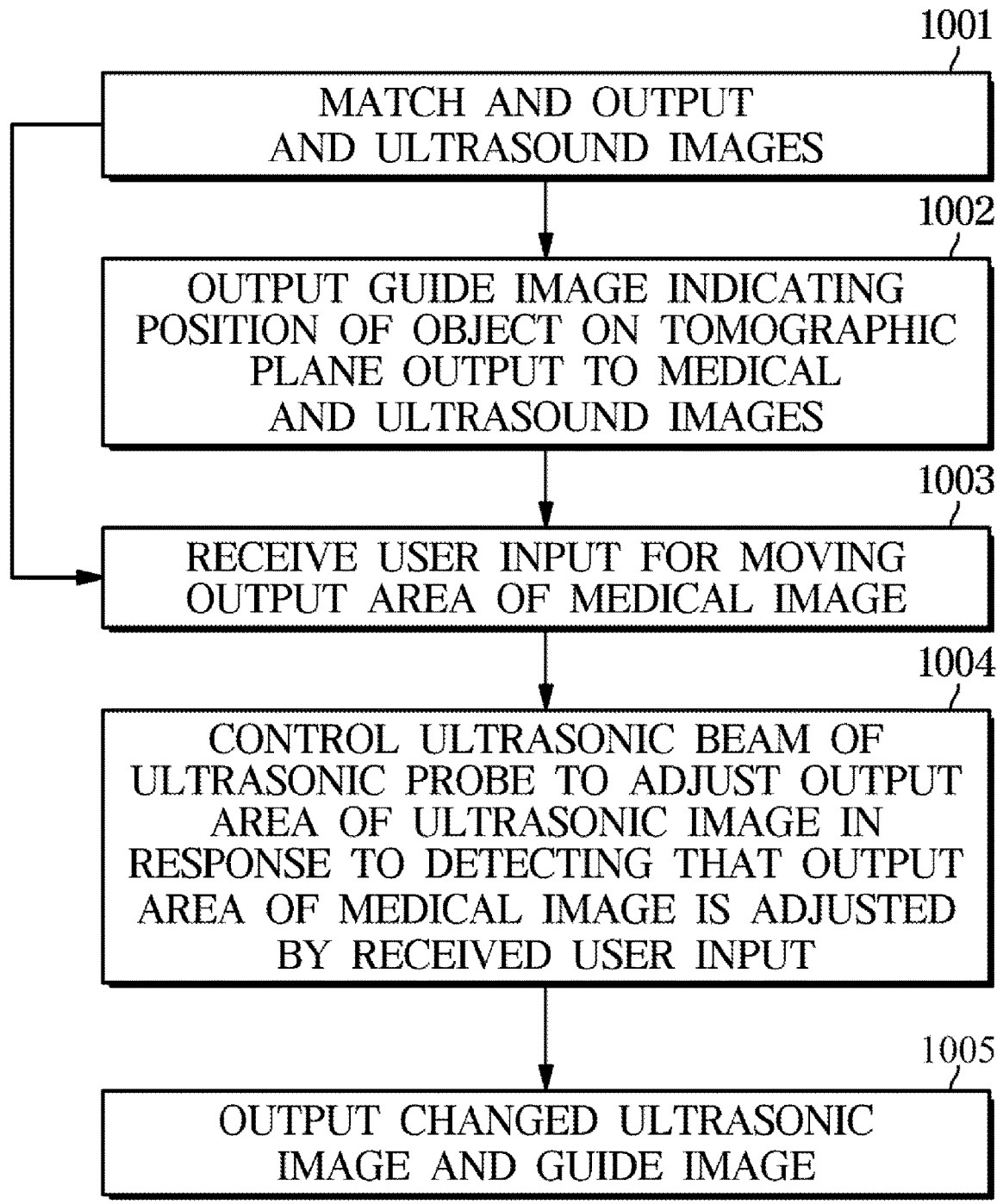
FIG. 11 is a flowchart illustrating a method of controlling an image according to embodiments of the disclosure.

FIG. 11 is a flowchart illustrating a method of controlling an image according to embodiments of the disclosure. However, this is merely exemplary and it should be understood that some of the operations may be added or omitted if desired.

A matching process is performed such that the medical image B and the ultrasound image A output the same tomography planes from the object, and the matched medical image B and the ultrasound image A may be output (1001).

Meanwhile, when matching between the medical image B and the ultrasound image A is performed, the guide image 2000 indicating the position of the object on the tomographic plane output to the medical image B and the ultrasound image A is output (1002). Detailed description of the guide image 2000 will be omitted as already described in detail with reference to FIGS. 5 to 9.

The user input for moving the output area of the medical image B is received (1003). Here, the user input may refer to the movement command for moving the position of the tomographic plane on the stored 3D volume data through the medical image B and outputting the moved tomographic plane to the medical image B.

When it is detected that the output area of the medical image B is adjusted by the user input, the ultrasonic beam of the ultrasonic probe 100 may be controlled to adjust the output area of the ultrasonic image A in response thereto (1004). In detail, the ultrasonic probe 100 may control the ultrasonic beam in the fixed state to the object so that the ultrasonic image A corresponds to the changed medical image.

When the ultrasound beam is controlled in operation 1004, the ultrasound image A may output another tomography plane of the object. As the output area of the medical image B is changed, the output area of the ultrasound image A may be changed, and the guide image 2000 having the changed position area 2100 may be output.

According to an aspect of the disclosure as described above, since the ultrasound image matched to the medical image in real time is provided, a lesion of interest can be effectively confirmed.

In addition, since the position of the object can be confirmed in real time through the guide image, a patient can be diagnosed efficiently and accurately.

Meanwhile, the disclosed embodiments may be implemented in the form of a recording medium storing instructions that are executable by a computer. The instructions may be stored in the form of a program code, and when executed by a processor, the instructions may generate a program module to perform operations of the disclosed embodiments. The recording medium may be implemented as a computer-readable recording medium.

The computer-readable recording medium may include all kinds of recording media storing commands that can be interpreted by a computer. For example, the computer-readable recording medium may be ROM, RAM, a magnetic tape, a magnetic disc, flash memory, an optical data storage device, etc.

The exemplary embodiments of the disclosure have thus far been described with reference to the accompanying drawings. It will be obvious to those of ordinary skill in the art that the disclosure may be practiced in other forms than the exemplary embodiments as described above without changing the technical idea or essential features of the disclosure. The above exemplary embodiments are only by way of example, and should not be interpreted in a limited sense.

What is claimed is:

1. An ultrasonic imaging apparatus comprising:
an ultrasonic probe configured to transmit an ultrasonic signal to an object and receive an echo signal reflected from the object;
a display configured to output an ultrasound image of the object output by the ultrasonic probe and a medical image which is a non-ultrasound image of the object stored in a memory and is obtained with an imaging modality different from that of the ultrasound image;
an inputter configured to receive a user input for adjusting a tomographic position of the medical image; and
a controller configured to, when the tomographic position of the medical image is adjusted by the user input, control an ultrasonic beam of the ultrasonic probe to adjust an output area of the ultrasound image corresponding to in response the adjusted tomographic position of the medical image,
wherein the display outputs, in real time, an ultrasonic image having the adjusted output area corresponding to the adjusted tomographic position of the medical image, as the controller controls only the ultrasonic beam while the ultrasonic probe is fixed to the object.

2. The ultrasonic imaging apparatus according to claim 1, wherein the controller is configured to control the ultrasound beam to move in a lateral direction when detecting the user input of moving the output area of the medical image in a left direction or a right direction.

3. The ultrasonic imaging apparatus according to claim 1, wherein the controller is configured to control an intensity of the ultrasound beam to adjust a depth of an axis direction when detecting the user input of moving the output area of the medical image in an upward direction or a downward direction.

4. The ultrasonic imaging apparatus according to claim 1, wherein the controller is configured to control the ultrasound beam to move or rotate in an elevation direction when detecting the user input of moving to an adjacent tomographic plane with respect to a tomographic plane of the output area of the medical image.

5. The ultrasonic imaging apparatus according to claim 1, wherein the controller is configured to control the ultrasound beam by changing at least one of element operation, steering, beam forming, and focusing of the ultrasonic probe.

6. The ultrasonic imaging apparatus according to claim 1, further comprising:
a storage configured to store the medical image,
wherein the medical image comprises at least one of Magnetic Resonance Imaging (MRI), Computerized Tomography (CT), Positron Emission Tomography (PET), and Single Photon Tomography Computed Tomography (SPECT) that three-dimensional (3D) volume image data.

7. The ultrasonic imaging apparatus according to claim 1, wherein the display is configured to output a guide image, and
wherein the controller is configured to generate the guide image in which an output limit range of the medical image of the object, an output limit range of the ultrasound image of the object, and a position area indicating a position of a current ultrasound image of the object are displayed.

8. The ultrasonic imaging apparatus according to claim 7, wherein, when a movement of the ultrasonic probe with respect to the object is detected, the controller is configured to change the position of the output limit range of the ultrasound image.

9. The ultrasonic imaging apparatus according to claim 7, wherein the controller is configured to generate a warning notification when the output area of the medical image according to the user input is an area that the ultrasonic probe cannot photograph.

10. The ultrasonic imaging apparatus according to claim 7, wherein the controller is configured to control the position area displayed on the guide image to be moved according to the user input of moving the output area of the medical image.

11. The ultrasonic imaging apparatus according to claim 10, wherein the controller is configured to control the position area to be moved along a lateral direction when the output area of the medical image moves in a left direction or a right direction.

12. The ultrasonic imaging apparatus according to claim 10, wherein the controller is configured to control the position area to be moved along an axial direction when the output area of the medical image moves upward or downward.

13. The ultrasonic imaging apparatus according to claim 10, wherein the controller is configured to control the position area to be moved or rotated in an elevation direction when the output area of the medical image moves an adjacent tomographic plane with respect to a tomographic plane.

14. A method of controlling an image performed by an ultrasonic imaging apparatus, the method comprising:
outputting an ultrasound image of an object output by an ultrasonic probe and a medical image which is a non-ultrasound image of the object stored in a memory and is obtained with an imaging modality different from that of the ultrasound image;
receiving a user input of moving a tomographic position of the medical image; and
when the tomographic position of the medical image is adjusted by the user input, controlling an ultrasonic beam of the ultrasonic probe to adjust an output area of the ultrasound image corresponding to the adjusted tomographic position of the medical image,
wherein the outputting of the ultrasound image includes outputting, in real time, an ultrasonic image having the adjusted output area corresponding to the adjusted tomographic position of the medical image, by controlling only the ultrasonic beam while the ultrasonic probe is fixed to the object.

15. The method according to claim 14, wherein the controlling of the ultrasonic beam comprises:
controlling the ultrasound beam to move in a lateral direction when detecting the user input of moving the output area of the medical image in a left direction or a right direction.

16. The method according to claim 14, wherein the controlling of the ultrasonic beam comprises:
controlling an intensity of the ultrasound beam to adjust a depth of an axis direction when detecting the user input of moving the output area of the medical image in an upward direction or a downward direction.

17. The method according to claim 14, wherein the controlling of the ultrasonic beam comprises:
controlling the ultrasound beam to move or rotate in an elevation direction when detecting the user input of moving to an adjacent tomographic plane with respect to a tomographic plane of the output area of the medical image.

18. The method according to claim 14, wherein the controlling of the ultrasonic beam comprises:

controlling the ultrasound beam by changing at least one of element operation, steering, beam forming, and focusing of the ultrasonic probe.

\* \* \* \* \*